United States Patent
Baldwin (10) Patent No.: US 6,248,735 B1
(45) Date of Patent: *Jun. 19, 2001

(54) OPHTHALMIC COMPOSITIONS COMPRISING COMBINATIONS OF A CARBONIC ANHYDRASE INHIBITOR AND A β-ADRENERGIC ANTAGONIST

(75) Inventor: John J. Baldwin, Gwynedd Valley, PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/833,067

(22) Filed: Apr. 3, 1997

Related U.S. Application Data (63) Continuation of application No. 08/587,698, filed on Jan. 17, 1996, now abandoned, which is a continuation of application No. 08/286,157, filed on Aug. 4, 1994, now abandoned.

(51) Int. Cl.$^7$ .................................................. A61K 31/535

(52) U.S. Cl. ...................... 514/226.5; 514/23.8; 514/913

(58) Field of Search ............................. 514/226.5, 235.8, 514/913

(56) References Cited

U.S. PATENT DOCUMENTS

| | | |
|---|---|---|
| 4,160,452 | 7/1979 | Theeuwes . |
| 4,195,085 | 3/1980 | Stone . |
| 4,256,108 | 3/1981 | Theeuwes . |
| 4,265,874 | 5/1981 | Berson et al. . |
| 4,287,175 | 9/1981 | Katz . |
| 4,386,098 | 5/1983 | Woltersdorf, Jr. et al. . |
| 4,416,890 | 11/1983 | Woltersdorf, Jr. . |
| 4,426,388 | 1/1984 | Woltersdorf, Jr. . |
| 4,668,697 | 5/1987 | Shepard et al. . |
| 4,861,760 | 8/1989 | Mazuel et al. . |
| 4,863,922 | 9/1989 | Baldwin et al. . |
| 5,932,572 * | 8/1999 | Dean et al. ........................ 514/226.5 |

FOREIGN PATENT DOCUMENTS

| | | |
|---|---|---|
| 077261 | 4/1983 | (EP) . |
| 91/15486 | 10/1991 | (WO) . |
| WO 93/16701 | 9/1993 | (WO) . |

OTHER PUBLICATIONS

Kass et al. *Arch. Ophthalmol.* 100 941–942 (1982).

Berson et al., *Am. J. Ophthalmology* 92 788–791 (1981).

Pfeiffer et al. Deutche Ophthal. Gesselschaft, DOG Baden–Baden, Sep. 23–26, 1990, Meeting Abstract.

Gunning et al., International Ophthalmology, 15, pp 11–12 &Abstract (1991).

Pfeiffer et al. Fortschr Ophthalmology, 88 pp 846–7 (1991).

Wang et al., Arch Ophthalmology, 108, pp 511–513 (1990).

STN International Karlsruhe, File Phar, AN=7469, Pub. Ltd; Abstract.

STN International Karlsruhe, File Phar, AN=3610, Pub. Ltd; Abstract.

* cited by examiner

Primary Examiner—Zohreh Fay
(74) Attorney, Agent, or Firm—Sylvia A. Ayler; Mark R. Daniel (57) ABSTRACT

Combinations of a β-adrenergic antagonist and a topical carbonic anhydrase inhibitor are particularly useful in the treatment of ocular hypertension, especially in patients insufficiently responsive to treatment with β-adrenergic antagonists.

27 Claims, 1 Drawing Sheet

FIG.1

OPHTHALMIC COMPOSITIONS COMPRISING COMBINATIONS OF A CARBONIC ANHYDRASE INHIBITOR AND A β-ADRENERGIC ANTAGONIST

This is a continuation of application Ser. No. 08/587,698 filed on Jan. 17, 1996, now abandoned, which is a continuation of application Ser. No. 08/286,157 filed Aug. 4, 1994, now abandoned.

SUMMARY OF THE INVENTION

This invention relates to novel ophthalmic compositions comprising a topical carbonic anhydrase inhibitor of structure:

wherein A, Z, $R^1$ and X are as hereinafter defined, or an ophthamologically acceptable salt thereof and a β-adrenergic antagonist selected from betaxolol, bufenolol, carteolol, levobunolol, metipranolol, and timolol, or an ophthalmologically acceptable salt thereof.

The invention is also concerned with the use of the novel ophthalmic compositions in the treatment of ocular hypertension.

More particularly, it relates to such ophthalmic combinations and their use in the treatment of ocular hypertension and glaucoma, wherein the β-adrenergic antagonist is 1-(tert-butylamino)-3-[(4-morpholino-1,2,5-thiadiazol-3-yl)oxy]-2-propanol, or an ophthalmologically acceptable salt thereof which name includes the (S)-(−)- and (R)-(+)-enantiomers and any mixtures thereof, including racemic material. The (S)-(−)-enantiomer is generally known as timolol.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

Many of the drugs formerly used to treat glaucoma proved not entirely satisfactory. The early methods of treatment of glaucoma employing pilocarpine produced undesirable local effects that made this drug, though valuable, unsatisfactory as a first line drug. More recently, clinicians have noted that many β-adrenergic antagonists are effective in reducing intraocular pressure. While many of these agents are effective for this purpose, there exist some patients with whom this treatment is not effective or not sufficiently effective. Many of these agents also have other characteristics, e.g., membrane stabilizing activity, that become more apparent with increased doses and render them unacceptable for chronic ocular use.

The β-adrenergic antagonist (S)-1-(tert-butylamino)-3-[(4-morpholino-1,2,5-thiadiazol-3-yl)oxy]-2-propanol, timolol, was found to reduce intraocular pressure and to be devoid of many unwanted side effects associated with pilocarpine and, in addition, to possess advantages over many other β-adrenergic antagonists, e.g., to be devoid of local anesthetic properties, to have a long duration of activity, and to display minimal loss of effect with increased duration of dosing.

Although pilocarpine and β-adrenergic antagonists reduce intraocular pressure, none of these drugs manifests its action by inhibiting the enzyme carbonic anhydrase, and thus they do not take advantage of reducing the contribution to aqueous humor formation made by the carbonic anhydrase pathway.

Agents referred to as carbonic anhydrase inhibitors block or impede this inflow pathway by inhibiting the enzyme carbonic anhydrase. While such carbonic anhydrase inhibitors are now used to treat intraocular pressure by systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective.

For several years, the desirability of directing the carbonic anhydrase inhibitor to only the desired ocular target tissue has been recognized. Because carbonic anhydrase inhibitors have a profound effect in altering basic physiological processes, the avoidance of a systemic route of administation serves to diminish, if not entirely eliminate, those side effects caused by inhibition of carbonic anhydrase such as metabolic acidosis, vomiting, numbness, tingling, general malaise and the like. Topically effective carbonic anhydrase inhibitors are disclosed in U.S. Pat. Nos. 4,386,098; 4,416,890; 4,426,388; 4,668,697; and 4,863,922 and PCT Publication WO 91/15486. As yet, no topically effective carbonic anhydrase inhibitors are generally available for clinical use.

Thus, when a carbonic anhydrase inhibitor is combined with a β-adrenergic antagonist, there is experienced an effect that reduces the intraocular pressure below that obtained by either medicament individually.

The activity of carbonic anhydrase inhibitors currently under development wanes 6 to 8 hours post-dose, meaning that as single agents these carbonic anhydrase inhibitors must be administered at least three times a day to maintain the desired lowering of intraocular pressure. The combination of this invention maintains the desired lowering of intraocular pressure for a full twelve hours. Because of this increased duration of action, the combination disclosed herein is effective when administered only twice a day. Patient compliance is anticipated to be greater with twice a day administration than with three times a day administration.

The use of oral carbonic anhydrase inhibitors in combination with the topical β-adrenergic antagonist timolol and the resulting multiplicity of their effects is disclosed in Berson et al., *American Journal of Ophthalmology* 1981, 92, 788–791. However, the combination of an oral carbonic anhydrase inhibitor with a topical β-adrenergic antagonist presents two disadvantages. The first disadvantage is that the systemic use of a carbonic anhydrase inhibitor inhibits carbonic anhydrase throughout the body and exerts the same profound negative effects on basic metabolism whether it is used alone or in combination with a topical β-adrenergic antagonist. Secondly, there is poor patient compliance with simultaneous administration of both an oral and topical medicament.

The combination disclosed herein is effective either by co-administration of the medicaments in one solution or as a combined therapy achieved by prior administration of either the carbonic anhydrase inhibitor or the β-adrenergic antagonist followed by administration of the other solution. The use of a single solution containing both active medicaments is preferred.

The combination of this invention is suggested in U.S. Pat. No. 4,863,922, but a precise formulation of the relative combination of medicaments to give effective reduction of intraocular pressure is neither taught nor disclosed therein.

There exists a patient population insufficiently responsive to available β-adrenergic antagonists who will benefit from the combination disclosed herein. Because of the combined effect of the β-adrenergic antagonist and the carbonic anhydrase inhibitor, these otherwise refractory patients can obtain a marked beneficial reduction in intraocular pressure from such a combination.

Furthermore, there exists a patient population who will benefit from a combination where the minimal dosage of one or both of the medicaments is employed, thus minimizing the possibility of the occurrence of undesirable effects of one or both of the medicaments which would be more likely to become apparent with chronic use at the higher dosage.

DETAILED DESCRIPTION OF THE INVENTION

The novel ophthalmic compositions of this invention comprise a therapeutically effective amount of a topical carbonic anhydrase inhibitor and a β-adrenergic antagonist. The topical carbonic anhydrase inhibitor of the novel composition has the structural formula:

or an ophthalmologically acceptable salt thereof wherein:
  A is carbon or nitrogen, preferably carbon;
  Z is —NHR or —OR;
  R is $C_{1-6}$ alkyl, either straight or branched chain, preferably $C_{2-4}$ alkyl such as ethyl, propyl or isobutyl;
  $R^1$ is
    (a) hydrogen,
    (b) $C_{1-3}$ alkyl, preferably methyl, ethyl or n-propyl, or
    (c) $C_{1-4}$ alkoxy-$C_{1-4}$ alkyl, preferably methoxypropyl; and
  X is —S(O)$_2$— or —C(O)$_2$—.

The carbon atoms to which Z and $R^1$ are bonded may be chiral. When named according to absolute configuration, e.g., (R,S) or (S,S), the first letter represents the chirality the carbon atom to which Z is bonded and the second letter represents the charality of A when A is carbon. The carbonic anhydrase inhibitors of this invention accordingly may be used as diastereomeric mixtures or single enantiomers or as racemic mixtures.

The β-adrenergic antagonist of the novel composition is selected from betaxolol, bufenolol, carteolol, levobunolol, metipranolol, and timolol, or an ophthalmologically acceptable salt thereof.

Most of the β-adrenergic antagonists and carbonic anhydrase inhibitors recited above have at least one asymmetric carbon atom and accordingly may exist as diastereomers or (+)- or (−)-enantiomers. This invention contemplates the use of any of the diastereomers or enantiomers or mixtures thereof including racemic forms.

The preferred β-adrenergic antagonist for use in the novel composition of this invention is timolol as its maleate salt.

The novel ophthalmic formulations of this invention comprise about 0.05 to 5% (w/w) of carbonic anhydrase inhibitor, usually about 0.5 to 3% (w/w) and about 0.01 to 1% (w/w) of β-adrenergic antagonist, preferably about 0.1 to 0.5% (w/w) to be administered on a 1 to 2 times a day schedule.

The novel method of this invention comprises the topical ocular administration of about 0.025 to 5 mg per day, preferably about 0.25 to 3 mg per day, of carbonic anhydrase inhibitor and concomitant, prior, or previous administration of about 0.005 to 1 mg per day, preferably about 0.05 to 0.5 mg per day, of β-adrenergic antagonist to each eye.

As a unit dosage, between 0.025 and 2.5 mg of the carbonic anhydrase inhibitor and 0.005 to 0.5 mg of the β-adrenergic antagonist are applied to the eye; preferably, 0.25 to 1.5 mg of the carbonic anhydrase inhibitor and 0.05 to 0.25 mg of the β-adrenergic antagonist.

Suitable subjects for the administration of the formulation of the present invention include primates, man and other animals, particularly man and domesticated animals such as cats and dogs.

For topical ocular administration the novel formulations of this invention may take the form of solutions, gels, ointments, suspensions or solid inserts, formulated so that a unit dosage comprises a therapeutically effective amount of each active component or some submultiple thereof.

Typical ophthalmologically acceptable carriers for the novel formulations are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, benzalkonium chloride, methyl and propyl paraben, benzyldodecinium bromide, benzyl alcohol, phenylethanol, buffering ingredients such as sodium chloride, sodium borate, sodium acetate, or gluconate buffers, and other conventional ingredients such as sorbitan monolaurate, triethanolamine, polyoxyethylene sorbitan monopalmitylate, dioctyl sodium sulfosuccinate, monothioglycerol, thiosorbitol, ethylenediamine tetra-acetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The formulation may also include a gum such as gellan gum at a concentration of 0.1 to 2% by weight so that the aqueous eyedrops gel on contact with the eye, thus providing the advantages of a solid ophthalmic insert as described in U.S. Pat. No. 4,861,760.

The pharmaceutical preparation may also be in the form of a solid insert such as one which after dispensing the drug remains essentially intact as described in U.S. Pat. Nos. 4,256,108; 4,160,452; and 4,265,874; or a bio-erodible insert that either is soluble in lacrimal fluids, or otherwise disintegrates as described in U.S. Pat. No. 4,287,175 or EPO publication 0,077,261.

The following examples of ophthalmic formulations are given by way of illustration.

EXAMPLE 1

| SOLUTION COMPOSITION | I | II | III |
|---|---|---|---|
| (S,S)-(-)-5,6-dihydro-4-ethyl-amino-6-methyl-4H-thieno-[2,3b]thiopyran-2-sulfonamide-7,7-dioxide monohydrochloride | 22.26 g | 22.26 g | 1.113 g |
| (S)-(-)-1-(tert-butylamino)-3-[(4-morpholino-1,2,5-thiadiazol-3-yl)oxy]-2-propanol maleate | 6.834 g | 1.367 g | 6.834 g |
| Sodium citrate.2H$_2$O | 2.940 g | 2.940 g | 2.940 g |
| Benzalkonium Chloride | 0.075 g | 0.075 g | 0.075 g |
| Hydroxyethylcellulose | 5.00 g | 5.00 g | 5.00 g |
| Sodium hydroxide q.s. | pH = 6.0 | pH = 6.0 | pH = 6.0 |
| Mannitol | 16.00 g | 21.00 g | 35.90 g |
| Water for injection q.s. ad. | 1000 g | 1000 g | 1000 g |

The active compounds, sodium citrate, benzalkonium chloride (in a 50% W/W solution), and mannitol are dissolved in approximately 400 mL water for injection in a tared and sterile vessel. The pH of the composition is adjusted to 6.0 by addition of 0.2 N sodium hydroxide solution, and water for injection is added until the weight of composition equals 750 g. The composition is sterilized by filtration, pushing the solution with a 2 bar pressure of 0.45 micron filtrated nitrogen. Then 250 g of a 2% hydroxyethylcellulose autoclaved solution is added and the obtained solution is homogenized by stirring with a magnetic stirring bar. The solution is aseptically subdivided into 3.5 mL aliquots and sealed.

EXAMPLE 2

| SOLUTION COMPOSITION | I | II | III |
|---|---|---|---|
| (S,S)-(-)-5,6-dihydro-4-ethyl-amino-6-methyl-4H-thieno-(2,3b]thiopyran-2-sulfonamide-7,7-dioxide | 1.0 mg | 1.5 mg | 0.5 mg |
| 4-[2-hydroxy-3-(1-methylethyl)-amino]-propoxy]-2,3,6-trimethylphenol-1-acetate | 0.3 mg | 0.2 mg | 0.4 mg |
| Monobasic sodium phosphate 2H$_2$O | | Quantity sufficient to give final pH 5.5–6.0 | |
| Dibasic sodium phosphate .12H$_2$O | | | |
| Benzalkonium chloride | 0.10 mg | 0.10 mg | 0.10 mg |
| Polysorbate 80 | 0.2 mg | 0.2 mg | 0.2 mg |
| Water for injection q.s. ad. | 1.0 mL | 1.0 mL | 1.0 mL |

The active compounds, phosphate buffer salts, benzalkonium chloride, and Polysorbate 80 are added to and suspended or dissolved in water. The pH of the composition is adjusted to 5.5–6.0 and diluted to volume. The composition is rendered sterile by filtration through a sterilizing filter.

EXAMPLE 3

| SOLUTION COMPOSITION | I | II |
|---|---|---|
| trans-5,6-dihydro-4-ethylamino-6-methyl-4H-thieno[2,3b]thiopyran-2-sulfonamide-7,7-dioxide | 1.7 mg | 0.8 mg |
| 1-[4-[2-(cyclopropylmethoxy)-ethyl]phenoxy]-3-(1-methylethyl)-amino]-2-propanol | 0.3 mg | 0.2 mg |
| Monobasic sodium phosphate.2H$_2$O | 9.5 mg | 9.5 mg |
| Dibasic sodium phosphate.12H$_2$O | 28.5 mg | 28.5 mg |
| Benzalkonium chloride | 0.10 mg | 0.10 mg |
| Sodium hydroxide q.s. ad. | pH 6.0 | pH 6.0 |
| Water for injection q.s. ad. | 1.0 mL | 1.0 mL |

The active compounds, phosphate buffer salts, and benzalkonium chloride are added to and dissolved in water. The pH of the composition is adjusted to 6.0 with sodium hydroxide and the final solution is diluted to volume. The solution is rendered sterile by filtration through a sterilizing filter.

EXAMPLE 4

| SOLUTION COMPOSITION | I | II | III |
|---|---|---|---|
| (S,S)-(-)-5,6-dihydro-4-propyl-amino-6-methoxypropyl-4H-thieno-[2,3b]thiopyran-2-sulfonamide-7,7-dioxide monohydrochloride | 21.0 g | 21.0 g | 1.5 g |
| (S)-(-)-1-(tert-butylamino)-3-[(4-morpholino-1,2,5-thiadiazol-3-yl)oxy]-2-propanol maleate | 6.8 g | 1.3 g | 6.8 g |
| Sodium citrate.2H$_2$O | 2.9 g | 2.9 g | 2.9 g |
| Benzalkonium Chloride | 0.075 g | 0.075 g | 0.075 g |
| Hydroxyethylcellulose | 5.0 g | 5.0 g | 5.0 g |
| Sodium hydroxide q.s. | pH = 6.0 | pH = 6.0 | pH = 6.0 |
| Mannitol | 35.9 g | 35.9 g | 35.9 g |
| Water for injection q.s. ad. | 1000 g | 1000 g | 1000 g |

The active compounds, sodium citrate, benzalkonium chloride (in a 50% W/W solution), and mannitol are dissolved in approximately 400 mL water for injection in a tared and sterile vessel. The pH of the composition is adjusted to 6.0 by addition of 0.2 N sodium hydroxide solution and water for injection is added until the weight of composition equals 750 g. The composition is sterilized by filtration, pushing the solution with a 2 bar pressure of 0.45 micron filtrated nitrogen. Then 250 g of a 2% hydroxyethylcellulose autoclaved solution is added and the obtained solution is homogenized by stirring with a magnetic stirring bar. The solution is aseptically subdivided into 3.5 mL aliquots and sealed.

EXAMPLE 5

| SOLUTION COMPOSITION | I | II | III |
|---|---|---|---|
| (S,S)-(-)-5,6-dihydro-4-propylamino-6-methoxypropyl-4H-thieno[2,3b]thiopyran-2-sulfonamide-7,7-dioxide | 1.0 mg | 1.5 mg | 0.5 mg |

-continued

| SOLUTION COMPOSITION | I | II | III |
|---|---|---|---|
| 4-[2-hydroxy-3-(1-methylethyl)-amino]propoxy]-2,3,6-trimethylphenol-1-acetate | 0.3 mg | 0.2 mg | 0.4 mg |
| Monobasic sodium phosphate .2H$_2$O | Quantity sufficient to give final pH 5.5–6.0 | | |
| Dibasic sodium phosphate .12H$_2$O | | | |
| Benzalkonium chloride | 0.10 mg | 0.10 mg | 0.10 mg |
| Polysorbate 80 | 0.2 mg | 0.2 mg | 0.2 mg |
| Water for injection q.s. ad. | 1.0 mL | 1.0 mL | 1.0 mL |

The active compounds, phosphate buffer salts, benzalkonium chloride, and Polysorbate 80 are added to and suspended or dissolved in water. The pH of the composition is adjusted to 5.5–6.0 and diluted to volume. The composition is rendered sterile by filtration through a sterilizing filter.

EXAMPLE 6

| SOLUTION COMOSITION | I | II |
|---|---|---|
| trans-5,6-digydro-4-propylamino-6-methoxypropyl-4H-thieno[2,3b]thiopyran-2-sulfonamide-7,7-dioxide | 1.7 mg | 0.8 mg |
| 1-[4-[2-(cyclopropylmethoxy)ethyl]-phenoxy]-3-(1-methylethyl)amino]-2-propanol | 0.3 mg | 0.2 mg |
| Monobasic sodium phosphate.2H$_2$O | 9.5 mg | 9.5 mg |
| Dibasic sodium phosphate.12H$_2$O | 28.5 mg | 28.5 mg |
| Benzalkonium chloride | 0.10 mg | 0.10 mg |
| Sodium hydroxide q.s. | pH 6.0 | pH 6.0 |
| Water for injection q.s. ad. | 1.0 mL | 1.0 mL |

The active compounds, phosphate buffer salts, and benzalkonium chloride are added to and dissolved in water. The pH of the composition is adjusted to 6.0 with sodium hydroxide and the final solution is diluted to volume. The solution is rendered sterile by filtration through a sterilizing filter.

EXAMPLE 7

| SOLUTION COMPOSITION | I | II | III |
|---|---|---|---|
| (S)-(+)-5,6-dihydro-4-isobutyl-amino-4H-thieno[2,3b]thiopyran-2-sulfonamide-7,7-dioxide mono-hydrochloride | 21.0 g | 21.0 g | 1.5 g |
| (S)-(-)-1-(tert-butylamino)-3-[(4-morpholino-1,2,5-thiadiazol-3-yl)oxy]-2-propanol maleate | 6.8 g | 1.3 g | 6.8 g |
| Sodium citrate.2H$_2$O | 2.9 g | 2.9 g | 2.9 g |
| Benzalkonium Chloride | 0.075 g | 0.075 g | 0.075 g |
| Hydroxyethylcellulose | 5.0 g | 5.0 g | 5.0 g |
| Sodium hydroxide q.s. | pH = 6.0 | pH = 6.0 | pH = 6.0 |
| Mannitol | 35.9 g | 35.9 g | 35.9 g |
| Water for injection q.s. ad. | 1000 g | 1000 g | 1000 g |

The active compounds, sodium citrate, benzalkonium chloride (in a 50% W/W solution), and mannitol are dissolved in approximately 400 mL water for injection in a tared and sterile vessel. The pH of the composition is adjusted to 6.0 by addition of 0.2 N sodium hydroxide solution and water for injection is added until the weight of composition equals 750 g. The composition is sterilized by filtration, pushing the solution with a 2 bar pressure of 0.45 micron filtrated nitrogen. Then 250 g of a 2% hydroxyethylcellulose autoclaved solution is added and the obtained solution is homogenized by stirring with a magnetic stirring bar. The solution is aseptically subdivided into 3.5 mL aliquots and sealed.

EXAMPLE 8

| SOLUTION COMPOSITION | I | II | III |
|---|---|---|---|
| (S)-(+)-5,6-dihydro-4-isobutyl-amino-4H-thieno[2,3b]thiopyran-2-sulfonamide-7,7-dioxide | 1.0 mg | 1.5 mg | 0.5 mg |
| 4-[2-hydroxy-3-(1-methylethyl)-amino]propoxyl-2,3,6-trimethylphenol-1-acetate | 0.3 mg | 0.2 mg | 0.4 mg |
| Monobasic sodium phosphate .2H$_2$O | Quantity sufficient to give final pH 5.5–6.0 | | |
| Dibasic sodium phosphate .12H$_2$O | | | |
| Benzalkonium chloride | 0.10 mg | 0.10 mg | 0.10 mg |
| Polysorbate 80 | 0.2 mg | 0.2 mg | 0.2 mg |
| Water for injection q.s. ad. | 1.0 mL | 1.0 mL | 1.0 mL |

The active compounds, phosphate buffer salts, benzalkonium chloride, and Polysorbate 80 are added to and suspended or dissolved in water. The pH of the composition is adjusted to 5.5–6.0 and diluted to volume. The composition is rendered sterile by filtration through a sterilizing filter.

EXAMPLE 9

| SOLUTION COMPOSITION | I | II |
|---|---|---|
| (S)-(+)-5,6-dihydro-4-isobutyl-amino-4H-thieno[2,3b]thiopyran-2-sulfonamide-7,7-dioxide | 1.7 mg | 0.8 mg |
| 1-[4-[2-(cyclopropylmethoxy)-ethyl]-phenoxy]-3-(1-methylethyl)-amino]-2-propanol | 0.3 mg | 0.2 mg |
| Monobasic sodium phosphate.2H$_2$O | 9.5 mg | 9.5 mg |
| Dibasic sodium phosphate.12H$_2$O | 28.5 mg | 28.5 mg |
| Benzalkonium chloride | 0.10 mg. | 0.10 mg |
| Sodium hydroxide q.s. | pH 6.0 | pH 6.0 |
| Water for injection q.s. ad. | 1.0 mL | 1.0 mL |

The active compounds, phosphate buffer salts, and benzalkonium chloride are added to and dissolved in water. The pH of the composition is adjusted to 6.0 with sodium hydroxide and the final solution is diluted to volume. The solution is rendered sterile by filtration through a sterilizing filter.

EXAMPLE 10

| SOLUTION CONPOSITION | I | II |
|---|---|---|
| (S,S)-(-)-5,6-dihydro-4-ethyl-amino-6-methyl-4H-thieno[2,3b]-thiopyran-2-sulfonamide-7,7-dioxide monohydrochloride | 2.0 mg | 0.2 mg |

-continued

| SOLUTION CONPOSITION | I | II |
|---|---|---|
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 11

| SOLUTION COMPOSITION | I | II |
|---|---|---|
| (S)-(+)-5,6-dihydro-4-isobutyl-amino-4H-thieno[2,3b]thiopyran-2-sulfonamide-7,7-dioxide | 3.0 mg | 0.5 mg |
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic sodium phosphate .2H$_2$O | Quantity sufficient to give | |
| Dibasic sodium phosphate .12H$_2$O | final pH 5.0–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.0–6.0 and diluted to volume. The composition is rendered sterile by ionizing radiation.

EXAMPLE 12

| SOLUTION COMPOSITION | I | II |
|---|---|---|
| (S,S)-(-)-5,6-dihydro-4-propyl-amino-6-methoxypropyl-4H-thieno[2,3b]thiopyran-2-sulfonamide-7,7-dioxide | 2.0 mg | 0.2 mg |
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 13

| SOLUTION COMPOSITION | I | II |
|---|---|---|
| (R)-(-)-5,6-dihydro-4-iso-butylamino-4H-thieno[2,3b]-thiopyran-2-sulfonamide-7,7-dioxide | 2.0 mg | 0.5 mg |
| 4-[2-hydroxy-3-(1-methylethyl)amino]propoxy]-2,3,6-trimethylphenol-1-acetate | 0.5 mg | 0.5 mg |
| GELRITE ™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 14

| SOLUTION COMPOSITION | I | II |
|---|---|---|
| cis-5,6-dihydro-4-ethylamino-6-methyl-4H-thieno[2,3b]thiopyran-2-sulfonamide-7,7-dioxide monohydrochloride | 2.0 mg | 0.2 mg |
| 4-[2-hydroxy-3-(1-methlethyl)-amino]propoxy]-2,3,6-trimethylphenol-l-acetate | 0.5 mg | 0.5 mg |
| GELRITE ™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 15

| SOLUTION COMPOSITION | I | II |
|---|---|---|
| cis-5,6-dihydro-4-propyl-amino-6-methoxypropyl-4H-thieno[2,3b]thiopyran-2-sulfonamide-7,7-dioxide | 2.0 mg | 0.5 mg |
| 4-[2-hydroxy-3-(1-methylethyl)-amino]propoxy]-2,3,6-trimethylphenol-1-acetate | 0.5 mg | 0.5 mg |
| GELRITE™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 16

| SOLUTION COMPOSITION | I | II |
|---|---|---|
| 5,6-dihydro-4-ethylamino-6-methyl-4H-thieno[2,3b]thiopyran-2-sulfonamide-7,7-dioxide monohydrochloride | 2.0 mg | 0.2 mg |
| 1-[4-[2-(cyclopropylmethoxy)ethyl]-phenoxy]-3-(1-methylethyl)amino]-2-propanol | 0.5 mg | 0.5 mg |
| GELRITE™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 17

| SOLUTION COMPOSITION | I | II |
|---|---|---|
| 5,6-dihydro-4-isobutylamino-4H-thieno[2,3b]thiopyran-2-sulfonamide-7,7-dioxide | 2.0 mg | 0.5 mg |
| 1-[4-[2-(cyclopropylmethoxy)ethyl]-phenoxy]-3-(1-methylethyl)amino]-2-propanol | 0.5 mg | 0.5 mg |
| GELRITE™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 18

| SOLUTION COMPOSITION | I | II |
|---|---|---|
| 5,6-dihydro-4-propylamino-6-methoxypropyl-4H-thieno[2,3b]thiopyran-2-sulfonamide-7,7-dioxide | 2.0 mg | 0.2 mg |
| 1-[4-[2-(cyclopropylmethoxy)ethyl]-phenoxy]-3-(1-methylethyl)amino]-2-propanol | 0.5 mg | 0.5 mg |
| GELRITE™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 19

| SOLUTION COMPOSITION | I | II | III |
|---|---|---|---|
| 3,4-Dihydro-4-methoxy-2-methyl-2H-thieno[3,2-e]-1,2-thiazine-6-sulfonamide-1,1-dioxide | 22.26 g | 22.26 g | 1.113 g |
| (S)-(-)-1-(tert-butylamino)-3-[(4-morpholino-1,2,5-thiadiazol-3-yl)oxy]-2-propanol maleate | 6.834 g | 1.367 g | 6.834 g |
| Sodium citrate.2H$_2$O | 2.940 g | 2.940 g | 2.940 g |
| Benzalkonium Chloride | 0.075 g | 0.075 g | 0.075 g |
| Hydroxyethylcellulose | 5.00 g | 5.00 g | 5.00 g |
| Sodium hydroxide q.s. | pH = 6.0 | pH = 6.0 | pH = 6.0 |
| Mannitol | 16.00 g | 21.00 g | 35.90 g |
| Water for injection q.s. ad. | 1000 g | 1000 g | 1000 g |

EXAMPLE 20

| SOLUTION COMPOSITION | I | II | III |
|---|---|---|---|
| 3,4-Dihydro-4-ethylamino-2-methyl-2H-thieno[3,2-e]-1,2-thiazine-6-sulfonamide-1,1-dioxide hydrochloride | 22.26 g | 22.26 g | 1.113 g |
| (S)-(-)-1-(tert-butylamino)-3-[(4-morpholino-1,2,5-thiadiazol-3-yl)oxy]-2-propanol maleate | 6.834 g | 1.367 g | 6.834 g |
| Sodium citrate.2H$_2$O | 2.940 g | 2.940 g | 2.940 g |
| Benzalkonium Chloride | 0.075 g | 0.075 g | 0.075 g |
| Hydroxyethylcellulose | 5.00 g | 5.00 g | 5.00 g |
| Sodium hydroxide q.s. | pH = 6.0 | pH = 6.0 | pH = 6.0 |
| Mannitol | 16.00 g | 21.00 g | 35.90 g |
| Water for injection q.s. ad. | 1000 g | 1000 g | 1000 g |

EXAMPLE 21

| SOLUTION COMPOSITION | I | II | III |
|---|---|---|---|
| 3,4-Dihydro-methyl-4-(2-methyl)propylamino-2H-thieno-[3,2-e]-1,2-thiazine-6-sulfonamide-1,1-dioxide hydrochloride | 22.26 g | 22.26 g | 1.113 g |
| (S)-(-)-1-(tert-butylamino)-3-[(4-morpholino-1,2,5-thiadiazol-3-yl)oxy]-2-propanol maleate | 6.834 g | 1.367 g | 6.834 g |
| Sodium citrate.2H$_2$O | 2.940 g | 2.940 g | 2.940 g |
| Benzalkonium Chloride | 0.075 g | 0.075 g | 0.075 g |
| Hydroxyethylcellulose | 5.00 g | 5.00 g | 5.00 g |
| Sodium hydroxide q.s. | pH = 6.0 | pH = 6.0 | pH = 6.0 |
| Mannitol | 16.00 g | 21.00 g | 35.90 g |
| Water for injection q.s. ad. | 1000 g | 1000 g | 1000 g |

EXAMPLE 22

| SOLUTION COMPOSITION | I | II | III |
|---|---|---|---|
| R-(+)-3,4-Dihydro-4-ethylamino-2-methyl)-2H-thieno[3,2-e]-1,2-thiazine-6-sulfonamide-1,1-dioxide hydrochloride | 22.26 g | 22.26 g | 1.113 g |
| (S)-(-)-1-(tert-butylamino)-3-[(4-morpholino-1,2,5-thiadiazol-3-yl)oxy]-2-propanol maleate | 6.834 g | 1.367 g | 6.834 g |
| Sodium citrate.2H$_2$O | 2.940 g | 2.940 g | 2.940 g |
| Benzalkonium Chloride | 0.075 g | 0.075 g | 0.075 g |
| Hydroxyethylcellulose | 5.00 g | 5.00 g | 5.00 g |
| Sodium hydroxide q.s. | pH = 6.0 | pH = 6.0 | pH = 6.0 |
| Mannitol | 16.00 g | 21.00 g | 35.90 g |
| Water for injection q.s. ad. | 1000 g | 1000 g | 1000 g |

EXAMPLE 23

| SOLUTION COMPOSITION | I | II | III |
|---|---|---|---|
| R-(+)-3,4-Dihydro-4-ethylamino-2-(2-methoxy)ethyl-2H-thieno-[3,2-e]-1,2-thiazine-6-sulfonamide-1,1-dioxide hydrochloride | 22.26 g | 22.26 g | 1.113 g |
| (S)-(-)-1-(tert-butylamino)-3-[(4morpholino-1,2,5-thiadiazol-3-yl)oxy]-2-propanol maleate | 6.834 g | 1.367 g | 6.834 g |
| Sodium citrate.2H$_2$O | 2.940 g | 2.940 g | 2.940 g |
| Benzalkonium Chloride | 0.075 g | 0.075 g | 0.075 g |
| Hydroxyethylcellulose | 5.00 g | 5.00 g | 5.00 g |
| Sodium hydroxide q.s. | pH = 6.0 | pH = 6.0 | pH = 6.0 |
| Mannitol | 16.00 g | 21.00 g | 35.90 g |
| Water for injection q.s. ad. | 1000 g | 1000 g | 1000 g |

EXAMPLE 24

| SOLUTION COMPOSITION | I | II | III |
|---|---|---|---|
| R-(+)-3,4-Dihydro-2-(2-methoxy)-ethyl-4-propylamino-2H-thieno-[3,2-e]-1,2-thiazine-6-sulfonamide-1,1-dioxide hydrochloride | 22.26 g | 22.26 g | 1.113 g |
| (S)-(-)-1-(tert-butylamino)-3-[(4-morpholino-1,2,5-thiadiazol-3-yl)oxy]-2-propanol maleate | 6.834 g | 1.367 g | 6.834 g |
| Sodium citrate.2H$_2$O | 2.946 g | 2.940 g | 2.940 g |
| Benzalkonium Chloride | 0.075 g | 0.075 g | 0.075 g |
| Hydroxyethylcellulose | 5.00 g | 5.00 g | 5.00 g |
| Sodium hydroxide q.s. | pH = 6.0 | pH = 6.0 | pH = 6.0 |
| Mannitol | 16.00 g | 21.00 g | 35.90 g |
| Water for injection q.s. ad. | 1000 g | 1000 g | 1000 g |

EXAMPLE 25

| SOLUTION COMPOSITION | I | II |
|---|---|---|
| 3,4-Dihydro-4-methoxy-2-methyl-2H-thieno[3,2-e]-1,2-thiazine-6-sulfonamide-1,1-dioxide | 2.0 mg | 0.2 mg |
| (S)-(-)-1-(tert-butylamino)-3-[(4-morpholino-1,2,5-thiadiazol-3-yl)oxy]-2-propanol maleate | 1.5 mg | 0.5 mg |
| GELRITE ™ gellan gum | 6.0 mg | 6.0 mg |
| Monobasic sodium phosphate .2H$_2$O | Quantity sufficient to give | |
| Dibasic sodium phosphate .12H$_2$O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 26

| SOLUTION COMPOSITION | I | II |
|---|---|---|
| 3,4-Dihydro-4-methylamino-2-methyl-2H-thieno[3,2-e]-1,2-thiazine-6-sulfonamide-1,1-dioxide hydrochloride | 2.0 mg | 0.2 mg |
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic sodium phosphate .2H₂O | Quantity sufficient to give | |
| Dibasic sodium phosphate .12H₂O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 27

| SOLUTION COMPOSITION | I | II |
|---|---|---|
| 3,4-Dihydro-2-methy-4-(2-methyl)propylamino-2H-thieno-[3,2-e]-1,2-thiazine-6-sulfonamide-1,1-dioxide hydrochloride | 2.0 mg | 0.2 mg |
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic sodium phosphate .2H₂O | Quantity sufficient to give | |
| Dibasic sodium phosphate .12H₂O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 28

| SOLUTION COMPOSITION | I | II |
|---|---|---|
| R-(+)-3,4-Dihydro-4-ethyl-amino-2-methyl-2H-thieno-[3,2-e]-1,2-thiazine-6-sulfonamide-1,1-dioxide hydrochloride | 2.0 mg | 0.2 mg |
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic sodium phosphate .2H₂O | Quantity sufficient to give | |
| Dibasic sodium phosphate .12H₂O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 29

| SOLUTION COMPOSITION | I | II |
|---|---|---|
| R-(+)-3,4-Dihydro-4-ethyl-amino-2-(2-methoxy)ethyl-2H-thieno[3,2-e]-1,2-thiazine-6-sulfonamide 1,1-dioxide hydrochloride | 2.0 mg | 0.2 mg |
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic sodium phosphate .2H₂O | Quantity sufficient to give | |
| Dibasic sodium phosphate .12H₂O | final pH 5.5–6.0 | |
| Benzyldodecinium bromide | 0.10 mg | 0.10 mg |
| polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 30

| SOLUTION COMPOSITION | I | II |
|---|---|---|
| R-(+)-3,4-Dihydro-2-(2-methoxy)-ethyl-4-propylamino-2H-thieno-[3,2-e]-1,2-thiazine-6-sulfonamide 1,1-dioxide hydrochloride- | 2.0 mg | 0.2 mg |
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic Sodium phosphate .2H₂O | Quantity sufficient to give | |
| Dibasic sodium phosphate .12H₂O | final pH 5.5–6.0 | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 31

| SOLUTION CONPOSITION | I | II | III |
|---|---|---|---|
| (S,S)-(-)-5,6-dihydro-4-ethyl-amino-6-propyl-4H-thieno-[2,3b]thiopyran-2-sulfonamide-7,7-dioxide monohydrochloride | 22.26 g | 22.26 g | 1.113 g |
| (S)-(-)-1-(tert-butylamino)-3-[(4-morpholino-1,2,5-thiadiazol-3-yl)oxy]-2-propanol maleate | 6.834 g | 1.367 g | 6.834 g |
| Sodium citrate.2H$_2$O | 2.940 g | 2.940 g | 2.940 g |
| Benzalkonium Chloride | 0.075 g | 0.075 g | 0.075 g |
| Hydroxyethylcellulose | 5.00 g | 5.00 g | 5.00 g |
| Sodium hydroxide q.s. | pH = 6.0 | pH = 6.0 | pH = 6.0 |
| Mannitol | 16.00 g | 21.00 g | 35.90 g |
| Water for injection q.s. ad. | 1000 g | 1000 g | 1000 g |

The active compounds, sodium citrate, benzalkonium chloride (in a 50% W/W solution), and mannitol are dissolved in approximately 400 mL water for injection in a tared and sterile vessel. The pH of the composition is adjusted to 6.0 by addition of 0.2 N sodium hydroxide solution, and water for injection is added until the weight of composition equals 750 g. The composition is sterilized by filtration, pushing the solution with a 2 bar pressure of 0.45 micron filtrated nitrogen. Then 250 g of a 2% hydroxyethylcellulose autoclaved solution is added and the obtained solution is homogenized by stirring with a magnetic stirring bar. The solution is aseptically subdivided into 3.5 mL aliquots and sealed.

EXAMPLE 32

| SOLUTION COMPOSITION | I | II |
|---|---|---|
| (S,S)-(-)-5,6-dihydro-4-ethyl-amino-6-propyl-4H-thieno-[2,3b]thiopyran-2-sulfonamide-7,7-dioxide monohydrochloride | 2.0 mg | 0.2 mg |
| (S)-(-)-1-(tert-butylamino)-3-[(4-morpholino-1,2,5-thiadiazol-3-yl)oxy]-2-propanol maleate | 0.5 mg | 0.5 mg |
| GELRITE ™ gellan gum | 6.0 mg | 6.0 mg |
| Monobasic sodium phosphate .2H$_2$O | Quantity sufficient to give final pH 5.5–6.0 | |
| Dibasic sodium phosphate .12H$_2$O | | |
| Benzyldodecinium bromide | 0.10 mg | 0.10 mg |
| Polysorbate 80 | 0.2 mg | 0.2 mg |
| Water for injection q.s. ad. | 1.0 mL | 1.0 mL |

The active compounds, GELRITE™ gellan gum, phosphate buffer salts, benzyldodecinium bromide and Polysorbate 80 are added to and suspended or dissolved in water. The pH of the composition is adjusted to 5.5–6.0 and diluted to volume. The composition is rendered sterile by ionizing radiation.

EXAMPLE 33

Study of (S,S)-(−)-5,6-dihydro-4-ethylamino-6-methyl-4H-thieno[2,3b]thiopyran-2-sulfonamide-7,7-dioxide (I) in combination with Timolol Patients aged 40 or over, with either ocular hypertension or primary open angle glaucoma with an intraocular pressure (IOP) in one or both eyes of 22 mmHg or more at one time point each day while receiving timolol 0.5% twice a day (bid) alone were admitted to the study. Patients had been on timolol 0.5% bid, either alone or in combination for at least three weeks prior to study entry and had been on timolol 0.5% bid as their sole glaucoma therapy for at least two weeks prior to study admission.

Secondary glaucoma was an exclusion as was a history of glaucoma surgery or laser trabeculoplasty/gonioplasty. Patients for whom timolol was contraindicated by the datasheet were excluded and also excluded were those on a concurrent β-blocker, carbonic anhydrase inhibitor, or clonidine. Thirty-one patients entered the study.

Procedure
1. All patients had their visual fields plotted by Goldmann Perimetry prior to study entry.
2. Patients were admitted for a 12 hour diurnal curve (i.e., IOP recorded at 08.00, 09.00, 10.00, 12.00, 14.00, 16.00, 18.00, 20.00 hours approximately, the 08.00 recording was immediately prior to instillation of the drops). All pressures were measured by the same observer using the same Goldmann applanation tonometer.
3. Following recording of the baseline Diurnal Curve on timolol 0.5% bid, all of the patients were. instructed to add 1 drop of a solution to each eye at 8:10 pm and 8:10 am, ten minutes after adding timolol, for seven days. The solution given to 16 of the patients contained 2% Compound I; the solution given to the other 15 patients was a placebo solution.
4. On Day 2, the IOP of each patient was measured at 8 am and 9 am, and a 12 hour diurnal curve was recorded on Day 8.

preliminary IOP data follow:

| MEAN IOP PRESTUDY AND PERCENT CHANGE IN IOP ON DAY 8 FROM PRESTUDY ||| 
|---|---|---|
| COMPOUND I PLUS TIMOLOL GROUP ||| 
| TIME | TIMOLOL BASELINE | TIMOLOL PLUS COMPOUND I |
| 8am | 27.4 | −16.8% |
| 9am | 27.1 | −21.0% |
| 10am | 25.4 | −18.9% |
| noon | 25.6 | −17.3% |
| 2pm | 24.5 | −18.6% |
| 4pm | 25.2 | −17.0% |
| 6pm | 25.7 | −18.2% |
| 8pm | 24.4 | −13.2% |
| PLACEBO PLUS TIMOLOL GROUP ||| 
| TIME | TIMOLOL BASELINE | TIMOLOL PLUS PLACEBO |
| 8am | 26.9 | −3.4% |
| 9am | 24.2 | −4.5% |
| 10am | 23.3 | −1.7% |
| noon | 23.2 | +0.2% |
| 2pm | 21.6 | +0.1% |
| 4pm | 22.7 | −0.1% |
| 6pm | 23.1 | −3.7% |
| 8pm | 21.9 | +6.6% |

Figure 1:
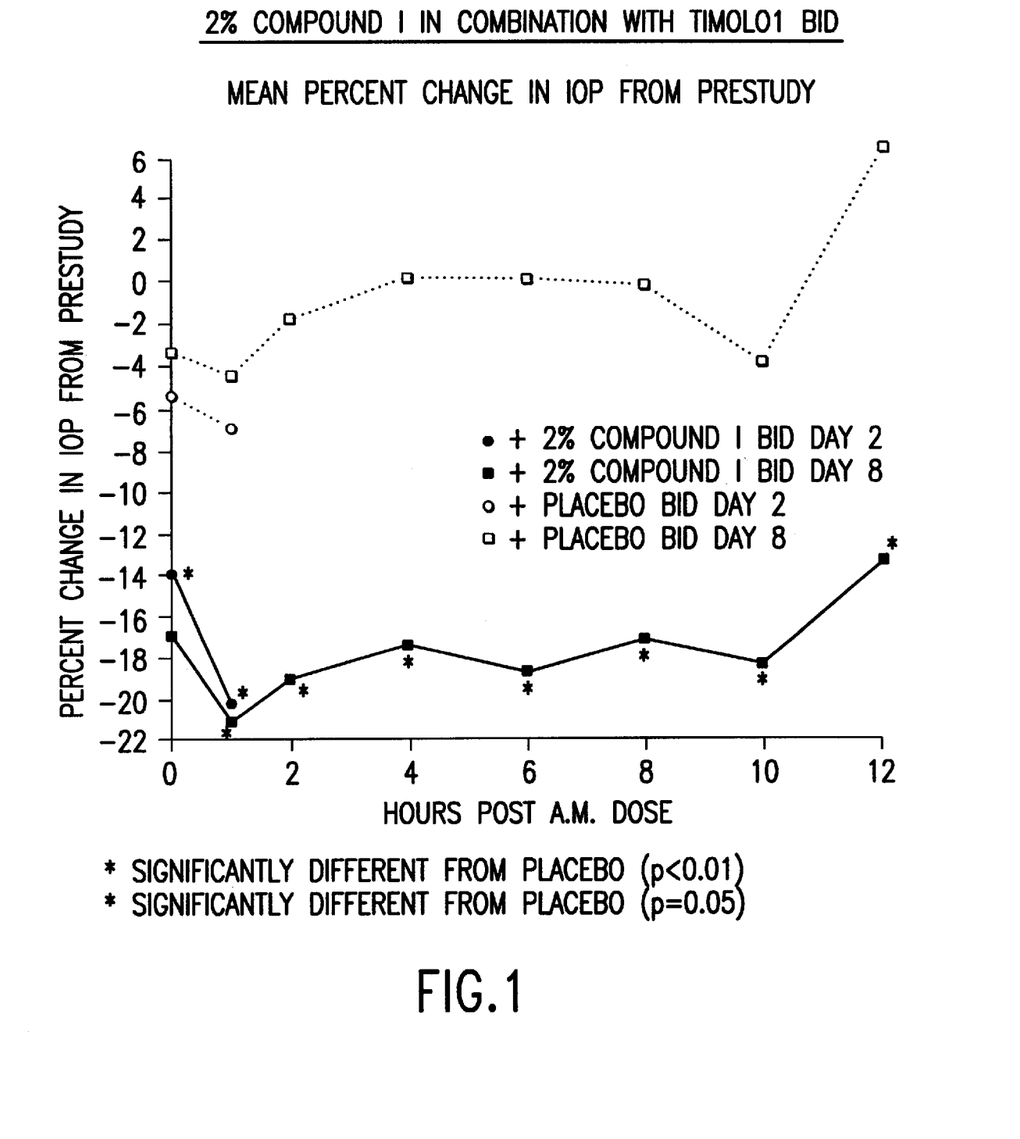
FIG. 1 shows percent change in intraocular pressure (10 p) from prestudy at hours post dose.

These data are represented graphically in Figure 1.

Overall, Compound I given every 12 hours demonstrated a clinically and statistically significant effect over the effect of timolol alone, ranging from 13%–21% based on worse eye analysis.

What is claimed is:

1. A topical formulation for treatment of ocular hypertension or glaucoma comprising an opthalmologically acceptable carrier, 0.05 to 5% of (S,S)-(–)-5,6-dihydro-4-ethylamino-6-methyl-4H-thieno-[2,3-b]thiopyran-2-sulfonamide-7,7 dioxide, the individual diastereomers, enantiomers or mixtures thereof, or an ophthalmologically acceptable salt thereof, and 0.01 to 1.0% of (s)-(–)-1-(tert-butylamino)-3-[(4-morpholino-1,2,5-thiadiazol-3-yl)oxy-2-propanol, or an ophthalmologically acceptable salt thereof.

2. A formulation of claim 1 wherein the salt of (s)-(–)-1-(tert-butylamino)-3-[(4-morpholino-1,2,5-thiadiazol-3-yl)oxy-2-propanol is maleate.

3. A formulation of claim 1 wherein the salt of (S,S)-(–)-5,6-dihydro-4-ethylamino-6-methyl-4H-thieno-[2,3-b]thiopyran-2-sulfonamide-7,7 dioxide is the monohydrochloride salt.

4. A formulation of claim 3 wherein the concentration of (S,S)-(–)-5,6-dihydro-4-ethylamino-6-methyl-4H-thieno-[2,3-b]thiopyran-2-sulfonamide-7,7 dioxide is 0.5 to 3%.

5. A formulation of claim 2 wherein the concentration of (s)-(–)-1-(tert-butylamino)-3-[(4-morpholino-1,2,5-thiadiazol-3-yl)oxy-2-propanol is 0.1 to 0.5%.

6. A formulation of claim 1 wherein the concentration of (S,S)-(–)-5,6-dihydro-4-ethylamino-6-methyl-4H-thieno-[2,3-b]thiopyran-2-sulfonamide-7,7 dioxide is 0.7 to 2.0% and the concentration of (s)-(–)-1-(tert-butylamino)-3-[(4-morpholino-1,2,5-thiadiazol-3-yl)oxy-2-propanol is 0.5%.

7. A formulation of claim 6 which further contains a gum.

8. A formulation of claim 7 wherein the gum is gellan gum at a concentration of 0.1% to 2%.

9. A formulation of claim 1 which takes a form of solution, gel, ointment, suspension or solid insert.

10. A formulation of claim 6 wherein the ratio of (S,S)-(–)-5,6-dihydro-4-ethylamino-6-methyl-4H-thieno-[2,3-b]thiopyran-2-sulfonamide-7,7 dioxide to (s)-(–)-1-(tert-butylamino)-3-[(4-morpholino-1,2,5-thiadiazol-3-yl)oxy-2-propanol is greater than one.

11. A formulation of claim 10 wherein the concentration of (S,S)-(–)-5,6-dihydro-4-ethylamino-6-methyl-4H-thieno-[2,3-b]thiopyran-2-sulfonamide-7,7 dioxide is 2% and (s)-(–)-1-(tert-butylamino)-3-[(4-morpholino-1,2,5-thiadiazol-3-yl)oxy-2-propanol is 0.5%.

12. A topical formulation for treatment of ocular hypertension or glaucoma comprising an opthalmologically acceptable carrier, 2% of (S,S)-(–)-5,6-dihydro-4-ethylamino-6-methyl-4H-thieno-[2,3-b]thiopyran-2-sulfonamide-7,7 dioxide monohydrochloride, and 0.5% of (s)-(–)-1-(tert-butylamino)-3-[(4-morpholino-1,2,5-thiadiazol-3-yl)oxy-2-propanol maleate, or an ophthalmologically acceptable salt thereof.

13. A formulation of claim 12 which further contains gellan gum at a concentration of 0.1% to 2%.

14. A method of treating ocular hypertension or glaucoma, which, comprises administration of an effective amount of a topical ophthalmic formulation to a patient in need thereof, comprising an ophthalmologically acceptable carrier, 0.05 to 5% of (S,S)-(–)-5,6dihydro-4-ethylamino-6-methyl-4H-thieno-[2,3-b]thiopyran-2-sulfonamide-7,7 dioxide, the individual diastereomers, enantiomers or mixtures thereof, or an ophthalmologically acceptable salt thereof, and 0.01 to 1.0% of (s)-(–)-1-(tert-butylamino)-3-[(4-morpholino-1,2,5-thiadiazol-3-yl)oxy-2-propanol, or an ophthalmologically acceptable salt thereof.

15. A method of claim 14 wherein the salt of (s)-(–)-1-(tert-butylamino)-3-[(4-morpholino-1,2,5-thiadiazol-3-yl)oxy-2-propanol is maleate.

16. A method of claim 14 wherein the salt of (S,S)-(–)-5,6-dihydro-4-ethylamino-6-methyl-4H-thieno-[2,3-b]thiopyran-2-sulfonamide-7,7 dioxide is the monohydrochloride salt.

17. A method of claim 16 wherein tie concentration of (S,S)-(–)-5,6-dihydro-4-ethylamino-6-methyl-4H-thieno-[2,3-b]thiopyran-2-sulfonamide-7,7 dioxide is 0.5 to 3%.

18. A method of claim 15 wherein the concentration of (s)-(–)-1-(tert-butylamino)-3-[(4-morpholino-1,2,5-thiadiazol-3-yl)oxy-2-propanol is 0.1 to 0.5%.

19. A method of claim 14 wherein the concentration of (S,S)-(–)-5,6-dihydro-4-ethylamino-6-methyl-4H-thieno-[2,3-b]thiopyran-2-sulfonamide-7,7 dioxide is 0.7 to 2.0% and the concentration of (s)-(–)-1-(tert-butylamino)-3-[(4-morpholino-1,2,5-thiadiazol-3-yl)oxy-2-propanol is 0.5%.

20. A method of claim 14 wherein the formulation contains a gum.

21. A method of claim 20 wherein the gum is gellan gum at a concentration of 0.1% to 2%.

22. A method of claim 14 wherein the formulation takes a form of solution, gel, ointment, suspension or solid insert.

23. A method of claim 14 wherein the formulation takes the form of a solution adapted for topical administration.

24. A method of claim 20 wherein the ratio of (S,S)-(–)-5,6-dihydro-4-ethylamino-6-methyl-4H-thieno-2,3-b]thiopyran-2-sulfonamide-7,7 dioxide to (s)-(–)-1-(tert-butylamino)-3-[(4-morpholino-1,2,5-thiadiazol-3-yl)oxy-2-propanol is greater than one.

25. A method of claim 14 wherein the concentration of (S,S)-(–)-5,6-dihydro-4-ethylamino-6-methyl-4H-thieno-[2,3-b]thiopyran-2-sulfonamide-7,7 dioxide is 2% and (s)-(–)-1-(tert-butylamino)-3-[(4-morpholino-1,2,5-thiadiazol-3-yl)oxy-2-propanol is 0.5%.

26. A method of treating ocular hypertension or glaucoma, which comprises administration of an effective amount of a topical ophthalmic formulation to a patient in need thereof, comprising an ophthalmologically acceptable carrier, 2% of (S,S)-(–)-5,6-dihydro-4-ethylamino-6-methyl-4H-thieno-[2,3-b]thiopyran-2-sulfonamide-7,7 dioxide monohydrochloride, 0.5% of (s)-(–)-1-(tert-butylamino)-3-[(4-morpholino-1,2,5-thiadiazol-3-yl)oxy-2-propanol maleate.

27. A method of claim 26 wherein the formulation contains gellan gum at a concentration of 0.1% to 2%.

* * * * *

UNITED STATES PATENT AND TRADEMARK OFFICE
CERTIFICATE OF CORRECTION

PATENT NO. : 6,248,735 B1  
DATED : June 19, 2001  
INVENTOR(S) : John J. Baldwin Page 1 of 1

It is certified that error appears in the above-identified patent and that said Letters Patent is hereby corrected as shown below:

<u>Title page,</u>
Related U.S. Application Data, insert --
    Continuation of USSN 08/587,698, filed on Jan 17, 1996, now abandoned, which is a continuation of application No. 08/286,157, filed on Aug. 4, 1994, now abandoned, which is a continuation of USSN 08/032,365, filed March 17, 1993, now abandoned, which is a continuation of USSN 07/834,913, filed Feb. 13, 1992, now abandoned, which is a continuation of USSN 07/686,718, filed April 17, 1991, now abandoned. --

Signed and Sealed this

Twenty-second Day of January, 2002

Attest:

*Attesting Officer*

JAMES E. ROGAN  
*Director of the United States Patent and Trademark Office*

UNITED STATES PATENT AND TRADEMARK OFFICE
CERTIFICATE OF CORRECTION

PATENT NO. : 6,248,735 B1
DATED : June 19, 2001
INVENTOR(S) : John J. Baldwin

It is certified that error appears in the above-identified patent and that said Letters Patent is hereby corrected as shown below:

<u>Title page,</u>
Related U.S. Application Data, insert --
    Continuation of USSN 08/587,698, filed on Jan 17, 1996, now abandoned, which is a continuation of application No. 08/286,157, filed on Aug. 4, 1994, now abandoned, which is a continuation of USSN 08/032,365, filed March 17, 1993, now abandoned, which is a continuation of USSN 07/834,913, filed Feb. 13, 1992, now abandoned, which is a continuation in-part of USSN 07/686,718, filed April 17, 1991, now abandoned. --

This certificate supersedes Certificate of Correction issued January 22, 2002.

Signed and Sealed this

Twenty-fifth Day of March, 2003

JAMES E. ROGAN
*Director of the United States Patent and Trademark Office*

Disclaimer

6,248,735—John J. Baldwin, Gwynedd Valley, PA (US) OPHTHALMIC COMPOSITIONS COMPRISING COMBINATIONS OF A CARBONIC ANHYDRASE INHIBITOR AND A β-ADRENERGIC ANTAGONONIST. Patent dated June 19, 2001. Disclaimer filed Apr. 21, 2006, by the Assignee, Merck & Co, Inc.

Hereby enters this disclaimer to claims 1-17,of said patent.

*(Official Gazette, June 27, 2006)*

Disclaimer

6,248,735 B1—John J. Baldwin, OPTHALMIC COMPOSTIONS COMPRISING COMBINATIONS OF A CARBONIC ANHYDRASE INHIBITOR AND A β-ADRENERGIC ANTAGONIST. Patent dated June 19, 2001. Disclaimer filed April 21, 2006, by the assignee, Merck & Co., Inc.

Hereby enters this disclaimer to claims 1-27, of said patent.

*(Official Gazette July 17, 2007)*